United States Patent [19]
Overstreet et al.

[11] Patent Number: 5,877,378
[45] Date of Patent: Mar. 2, 1999

[54] PROCESS FOR SELECTIVE UTILIZATION OF ALPHA-OLEFINS IN MIXTURES CONTAINING NON-ALPHA-OLEFINS

[75] Inventors: Andrew D. Overstreet; Robert H. Allen, both of Baton Rouge, La.; Larry H. Nemec, Houston, Tex.; Ronny W. Lin, Baton Rouge, La.

[73] Assignee: Amoco Corporation, Chicago, Ill.

[21] Appl. No.: 937,283

[22] Filed: Sep. 15, 1997

Related U.S. Application Data

[63] Continuation of Ser. No. 490,266, Jun. 14, 1995, abandoned.

[51] Int. Cl.$^6$ .............................. C07C 2/88; C07C 7/448; C07F 5/06
[52] U.S. Cl. .......................... 585/637; 585/328; 585/809; 556/190; 556/187
[58] Field of Search .................................. 585/328, 637, 585/809; 556/190, 187

[56] References Cited

U.S. PATENT DOCUMENTS

| | | | |
|---|---|---|---|
| 3,240,838 | 3/1966 | White et al. | 260/683.2 |
| 3,282,974 | 11/1966 | Bruno et al. | 260/448 |
| 3,285,988 | 11/1966 | Boyer | 260/677 |
| 3,291,853 | 12/1966 | Feighner et al. | 260/677 |
| 3,686,250 | 8/1972 | Lanier | 260/448 A |
| 4,918,254 | 4/1990 | Diefenback et al. | 585/328 |
| 5,124,465 | 6/1992 | Allen et al. | 556/190 |
| 5,278,330 | 1/1994 | Lin et al. | 556/190 |

*Primary Examiner*—Glenn Caldarola
*Assistant Examiner*—Thuan D. Dang
*Attorney, Agent, or Firm*—James R. Henes; Stephen L. Hensley

[57] ABSTRACT

The alpha-olefin content of mixed hydrocarbon streams is selectively utilized to produce trialkylaluminum compounds in which the alkyl groups are linear primary alkyl groups. This selective utilization is accomplished by use of a specific, highly selective low residence-time, low isomerization catalytic displacement reaction. In addition, when alpha-olefins are the desired end product, a second low residence-time catalytic displacement reaction is utilized whereby high purity alpha olefins are produced.

14 Claims, 1 Drawing Sheet

PROCESS FOR SELECTIVE UTILIZATION OF ALPHA-OLEFINS IN MIXTURES CONTAINING NON-ALPHA-OLEFINS

This is a continuation of application Ser. No. 08/490,266, filed Jun. 14, 1995, now abandoned.

TECHNICAL FIELD

This invention relates to selectively upgrading the alpha-olefin content of hydrocarbon mixtures containing both alpha-olefins and non-alpha olefins, such as mixtures which contain at least alpha-olefins, internal olefins and paraffins, and which may also contain naphthenes and/or aromatics.

BACKGROUND

It has long been recognized that the alpha-olefin content of various industrial hydrocarbon streams constitutes a valuable resource if the alpha-olefins can be suitably separated or recovered from the non-alpha-olefins with which they are associated. These streams may and often do contain close boiling isomers of alpha-olefins and internal olefins, along with paraffinic and/or other hydrocarbons such as naphthenes and aromatics.

In Boyer, U.S. Pat. No. 3,285,988, a process for recovering olefins from a mixed fluid stream is described. The process involves a pair of aluminum alkyl displacement reactions. In the first reaction the alpha-olefin-containing stream is reacted with trialkylaluminum in which at least one alkyl group contains from 2 to 4 carbon atoms, specifically triisobutylaluminum, at a temperature in the range of about 50° to 300° F. and for reaction times of at least 15 minutes, and preferably at least one-half hour. The resultant high molecular weight aluminum alkyl is recovered and subjected to a displacement reaction with a lower olefin, specifically isobutene, to release the alpha-olefins. It is indicated that in this reaction a catalyst, such as nickel or a nickel compound or cobalt, is usually used.

Feighner et al. U.S. Pat. No. 3,291,853 describes another process for accomplishing such separations. In this case the mixed stream is heated with a dialkylaluminum hydride at 80° to 130° C. so that the alpha-olefins react with the dialkylaluminum hydride to produce a reaction mass containing trialkylaluminum. The recovered trialkylaluminum is then heated to a temperature at which it decomposes to produce dialkylaluminum hydride and alpha-olefin.

A desirable contribution to the art would be novel, economically viable process technology whereby selective utilization of the alpha olefins present in a mixed hydrocarbon stream can be accomplished. This invention is deemed to constitute such a contribution.

SUMMARY OF THE INVENTION

In accordance with this invention process technology is provided which enables the alpha-olefin content of mixed hydrocarbon streams to be selectively utilized to produce trialkylaluminum compounds in which the alkyl groups are linear primary alkyl groups. Moreover, pursuant to this invention such selective utilization is accomplished by use of a specific, highly selective low residence-time, low isomerization catalytic displacement reaction. In addition, when alpha-olefins are the desired end product, a second low residence-time catalytic displacement reaction is utilized whereby high purity alpha olefins are produced.

Thus one of the embodiments of this invention is a process of selectively upgrading linear alpha-olefins contained in a mixture of liquid hydrocarbons. The process comprises admixing (i) a hydrocarbon feed comprising at least linear alpha-olefins and internal olefins, and (ii) tri-n-propylaluminum in the presence of a nickel or cobalt displacement catalyst under low residence-time, low isomerization displacement conditions that produce (iii) propylene, (iv) an alkyl aluminum product enriched in primary linear alkyl groups derived from said linear alpha-olefins, and (v) a hydrocarbon mixture enriched in hydrocarbons other than linear alpha-olefins, including olefins other than linear alpha-olefins.

In another embodiment where linear alpha-olefins are desired as an end product, this invention provides a process in which (iv) above, i.e., the alkyl aluminum product enriched in primary linear alkyl groups, is reacted with propylene in the presence of a nickel or cobalt displacement catalyst under low residence-time, low isomerization displacement conditions that produce (vi) tri-n-propylaluminum and (vii) linear alpha-olefins, and separating (vi) and (vii).

FURTHER DESCRIPTION OF THE INVENTION

Figure 1:
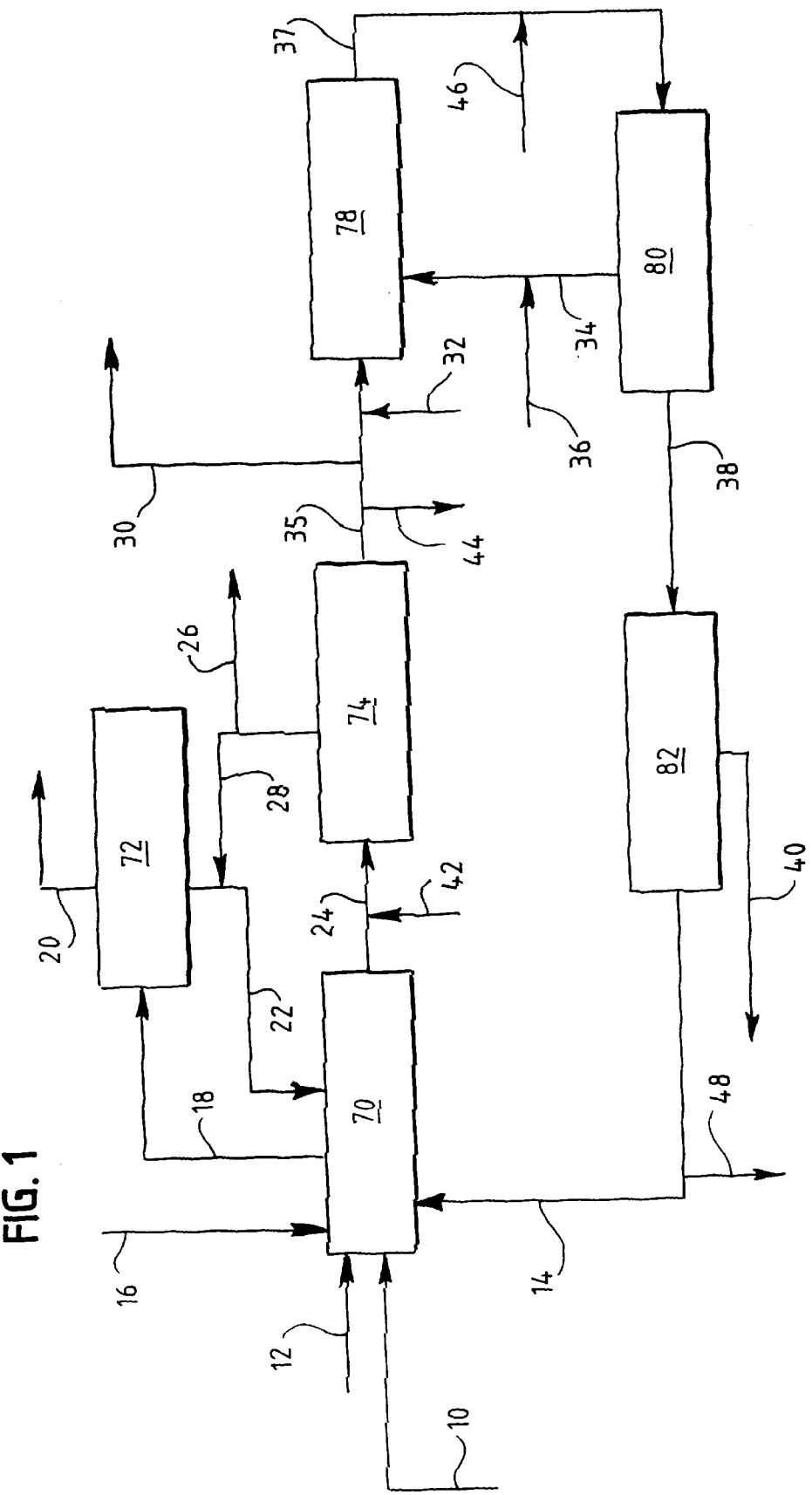
FIG. 1 is a schematic flow diagram of a preferred process of this invention for selective recovery of linear alpha-olefins from a mixed hydrocarbon stream.

In a first principal embodiment, this invention makes possible the synthesis of trialkylaluminum compounds in which substantially all of the alkyl groups are linear primary alkyl groups from mixtures of hydrocarbons which comprise both linear alpha-olefins and olefins other than linear alpha-olefins. If desired, these aluminum compounds can be subjected to controlled oxidation and hydrolysis using known conditions to produce linear primary alcohols.

Where it is desired to produce linear alpha-olefins as the end product, a second principal embodiment of this invention in effect selectively separates the alpha-olefins from a hydrocarbon mixture by chemical means.

Both of these embodiments will now be described with reference to FIG. 1, which illustrates preferred Integrated operations. Hydrocarbon feedstock containing linear alpha-olefins at 10, nickel or cobalt displacement catalyst at 12 and tri-n-propylaluminum at 14 are fed to displacement reactor 70 in which a low residence-time, low isomerization displacement reaction is conducted. In the flow arrangement shown in FIG. 1, the tri-n-propylaluminum feed 14 is a recycle stream referred to hereinafter, and makeup tri-n-propylaluminum at 16 is fed to reactor 70 as needed. The overhead 18 from reactor 70, mainly propylene along with some other relatively volatile hydrocarbons, is fed to propylene recovery unit 72 in which the propylene at 20 is separated for recycle. The other hydrocarbons from 72 can be recycled as at 22 if their composition justifies their inclusion in the displacement reaction conducted in reactor 70. Otherwise those hydrocarbons can be used for other purposes such as for their fuel value. The heavier effluent stream 24 from reactor 70, comprised of aluminum alkyl enriched in linear primary alpha-olefins and heavier hydrocarbons, is fed to unit 74 wherein the aluminum alkyls are separated from at least a portion of the hydrocarbons. If the composition of the hydrocarbons warrants recovery for purposes other than as fuel, unwanted hydrocarbons 26 can be purged and olefin stream 28 can be recycled to reactor 70.

Although depicted for ease of reference as a single reactor, 70 may be, for example, a series of stirred tank reactors with continuous removal of propylene.

If highly pure linear primary aluminum alkyls are desired for isolation or other uses, the aluminum alkyls in stream 35 from unit 74 can be recovered as a purge 30 from stream 35 following the removal as at 44 of lead/nickel or lead/cobalt (e.g., by filtration) as described hereinafter.

When linear alpha-olefins are the desired product, the second above embodiment is used. In this case, and still referring to FIG. 1, stream 35 containing the aluminum alkyls 30 is fed to reactor 78 in which the aluminum alkyls are reacted with propylene under low residence-time, low isomerization displacement conditions in the presence of a nickel or cobalt displacement catalyst, introduced as at 32. In the preferred arrangement depicted, the effluent 37 from reactor 78—which comprises a mixture of tri-n-propylaluminum, unreacted propylene and displaced olefins enriched in linear alpha-olefins—is fed to propylene recovery unit 80 and the propylene recovered in unit 80 is recycled as at 34 to reactor 78 along with makeup propylene at 36. Effluent 38 from unit 80, a mixture of tri-n-propylaluminum and displaced olefins enriched in linear alpha-olefins, is fed to column 82 wherein the olefins 40 and the tri-n-propylaluminum are separated from each other. The tri-n-propylaluminum is then used as the feed 14 to reactor 70.

The hydrocarbon mixtures used as feedstock in both principal embodiments contain linear alpha-olefins and liquid hydrocarbons other than linear alpha-olefins, such as internal olefins, paraffins, naphthenes, and/or aromatics. While hydrocarbon streams containing small amounts of linear alpha-olefins (e.g., 10% by volume) can be used, from a cost-effectiveness viewpoint the feedstock should contain at least 30% by volume, and preferably at least 40% by volume, of linear alpha-olefins. Such streams will also contain at least non-alpha-olefins. Raffinate streams from petroleum processing which contain at least 40% by volume of 1-butene is one preferred feedstock for recovery of the 1-butene therefrom. Another preferred feedstock is a 1-hexene-enriched $C_6$ fraction from a Fischer-Tropsch plant. Such streams can contain at least 50% or even as much as 60% of 1-hexene along with other hexene isomers.

The selective transformation of the alpha-olefins present in the mixed hydrocarbon feedstock into an alkyl aluminum product enriched in primary linear alkyl groups of type that takes place in reactor 70 involves contacting the olefins with tri-n-propylaluminum in the presence of a nickel or cobalt displacement catalyst under low residence-time, low isomerization displacement conditions. By the term "enriched" in connection with this unit operation is meant that at least 99% of the alkyl groups on the resultant aluminum alkyl product are linear primary alkyl groups.

The nickel or cobalt displacement catalysts which are included in the displacement reaction mixture in reactor 70 (and in reactor 78 when producing linear alpha-olefins) are compounds or complexes of nickel or cobalt. Mixtures of suitable nickel and cobalt compounds can be used, if desired. Preferably the nickel or cobalt compounds are sufficiently soluble in organic media, such as hydrocarbons, so that they perform as homogeneous catalysts. However it is possible, though less preferable, to employ heterogeneous nickel and/or cobalt catalysts such as colloidal forms of the metals themselves or relatively hydrocarbon-insoluble inorganic compounds thereof, which may be fixed on suitable supports. These displacement catalyst materials are exemplified by such nickel compounds as nickel carboxylates such as nickel naphthenate and nickel stearate, nickel bis (acetylacetonate), nickelocene, bis(1,5-cyclooctadiene)-nickel, nickel octylacetoacetate complex, nickel ethylenediamine tetraacetic acid complex, and similar nickel compounds or complexes. Examples of suitable cobalt compounds include cobalt carboxylates such as cobalt naphthenate and cobalt oleate, cobalt bis(acetylacetonate), cobaltacene, cobalt octylacetoacetate complex, cobalt ethylenediamine tetraacetic acid complex and like substances. The nickel catalysts have a greater tendency than the cobalt catalysts to cause isomerization of alpha-olefins. Thus trace amounts of soluble lead (II) compound may be included when using the nickel displacement catalysts to inhibit this isomerization tendency of the nickel catalyst.

Amounts of the displacement catalyst typically fall in the range equivalent to about 1 to about 100 parts by weight of nickel and/or cobalt per million parts of reaction mixture. However, amounts outside of this range can be used whenever deemed necessary or desirable under any given set of circumstances under consideration.

The low residence-time, low isomerization conditions of the displacement operation such as conducted in reactor 70 involve use of temperatures in the range of about 0° to about 100° C., and preferably temperatures in the range of 20° to 40° C., pressures in the range of 10 to about 200 psia, and reaction times of less than about 5 minutes (preferably about 1 to 3 minutes).

It is desirable, especially when the displacement catalyst used is a nickel catalyst, to deactivate the catalyst by use of a deactivating amount of a catalyst deactivator, preferably a hydrocarbon-soluble lead (II) compound. The use of a lead compound to deactivate the nickel or cobalt displacement catalyst precludes the possibility of undesired side reactions such as isomerization, oligomerization or polymerization from occurring. Suitable lead compounds include lead carboxylate salts, lead chelates or complexes, and organolead compounds such as tetraethyllead. Preferred materials include lead acetate, lead hexanoate, lead octanoate, lead 2-ethylhexanoate, lead naphthenate, and similar lead carboxylates; and lead chelates such as lead acetylacetonate and lead octylacetoacetate. The amount used should be an amount sufficient to deactivate the nickel or cobalt catalyst. Typically the amount will be sufficient to provide an Pb:Ni or Pb:Co atom ratio in the range of about 0.5:1 to about 5:1.

With reference to FIG. 1, the catalyst deactivator for the displacement catalyst used in the displacement reaction conducted in reactor 70 may be introduced at 42.

The catalyst deactivation is performed at any suitable temperature within the range of about 20° to about 150° C., and preferably within the range of about 50° to about 70° C. It is desirable to agitate the mixture or otherwise ensure good contact between the lead catalyst deactivator and the nickel or cobalt catalyst.

Inasmuch as the catalyst deactivator causes no harm to the aluminum alkyl formed in the displacement reaction, the deactivator can be carried through unit 74 and the resultant solids from the deactivation can be discharged as at 44. However if desired, the solids can be removed before passing the treated reaction product mixture to unit 74. Alternatively, a thermal agglomeration/conglomeration operation may be conducted wherein the treated reaction product may be transferred to a vessel (not depicted) wherein the product mixture after addition of the catalyst deactivator is stirred or otherwise agitated at a temperature in the range of about 50° to about 70° C. for a period of at least about 2 minutes. The agglomerated/conglomerated solids are then removed from the reaction mixture by any suitable procedure such as filtration, decantation, or centrifugation.

Propylene recovery in unit 72 typically involves use of a conventional distillation column, typically operating at 300 psia.

Unit 74 is typically a distillation column operating at 50 psia. It is desirable to use a low residence time reboiler to minimize aluminum alkyl degradation. Alternatively, one or a series of reboiled flashes may be used alone or in combination with the distillation column.

The displacement reaction such as performed in reactor 78 is also a low residence-time, low isomerization displacement reaction. The conditions for this reaction involve temperatures in the range of about −20° to about 100° C., and preferably in the range of 20° to 40° C. The aluminum alkyl feed to the displacement reaction can be pretreated with 1-olefin to remove any aluminum hydride so as to extend catalyst life. Pressures are typically in the range of about 100 to about 300 psia, with reaction times of from 0.5 to about 10 minutes and preferably from 2 to 7 minutes. The displacement catalysts and their usage are as described above with reference to the first displacement reaction such as conducted in reactor 70. It is not necessary, however, to use the identical materials or conditions in these two displacement reactions. Here again, use of catalyst deactivating amount of a lead (II) compound as catalyst deactivator is desirable. The deactivator may be introduced, for example, as at 46 and the solids removed as at 48. Agglomeration/conglomeration procedures such as described above can be utilized here also.

Propylene recovery in unit 80 typically involves use of a conventional distillation column, typically operating at 300 psia. Preliminary reboiled flashed flashing may also be used in combination with the distillation.

The conditions used in column 82 to separate the tri-n-propylaluminum and the alpha-olefin product from each other will of course depend to some extent on the makeup of the olefins in the alpha-olefin-tri-n-propylaluminum mixture. Olefins more volatile than tri-n-propylaluminum will be taken off overhead whereas olefins having higher boiling points than tri-n-propylaluminum will be taken off as column bottoms. Product olefins from column 82 can be subjected to further purification in any case where deemed necessary or desirable. However, this is a discretionary matter as it depends on the composition of the particular feedstock and the type and purity of product alpha-olefin desired.

It will be appreciated that the process described above with reference to FIG. 1 can be conducted as a series of batch or semi-batch operations, or as a continuous process.

There are a number of preferred extra features which can be used in the practice of a process such as depicted in FIG. 1. Among such features is using the recovered propylene at 20 as raw material for conversion to tri-n-propylaluminum for use in the displacement conducted in reactor 70. Another such feature is to use recovered propylene at 20 as makeup propylene feed at 36 to reactor 78.

Still another preferred embodiment can be utilized where the initial hydrocarbon mixture to be processed is a mixture that comprises at least linear alpha-olefins, internal olefins and vinylidene olefins. To enhance the recovery of pure linear alpha-olefins, the hydrocarbon mixture is subjected to a preliminary selective isomerization step wherein vinylidene olefins in the mixture are converted into tri-substituted olefins which are much less reactive with tri-n-propylaluminum and thus do not participate in the displacement reaction in reactor 70. Thus the aluminum alkyl product formed in that displacement operation contains trialkylaluminum in which the alkyl groups are enriched in linear primary alkyl groups derived from the linear alpha-olefins in the initial hydrocarbon mixture. Processing operations and conditions used in conducting the preliminary selective isomerization step can be those described in U.S. Pat. No. 3,686,250, the entire disclosure of which is incorporated herein by reference.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

We claim:

1. A process of selectively separating linear alpha-olefins contained in a mixture of liquid hydrocarbons, said process comprising admixing (i) a hydrocarbon feed comprising at least linear alpha-olefins and internal olefins, at least some of which have boiling temperatures proximate to that of at least some of said alpha-olefins and (ii) tri-n-propylaluminum in the presence of a nickel or cobalt displacement catalyst under low residence-time, low isomerization displacement conditions comprising a reaction temperature in the range of 20° to 40° C. and a reaction time of less than 5 minutes, that selectively produce (iii) propylene, (iv) an alkyl aluminum product enriched in primary linear alkyl groups derived from linear alpha-olefins in said feed, and (v) a hydrocarbon mixture enriched in internal olefins, without isomerizing the internal olefins to alpha olefins.

2. A process according to claim 1 wherein said hydrocarbon feed is a raffinate stream containing a substantial proportion of 1-butene.

3. A process according to claim 1 wherein said hydrocarbon feed is a hydrocarbon fraction from a Fischer-Tropsch process that contains a substantial proportion of at least one 1-olefin having in the range of about 5 to about 10 carbon atoms.

4. A process according to claim 1 wherein propylene formed in the process is recovered and converted into tri-n-propyl aluminum for use in the process.

5. The process according to claim 1 wherein said alkyl aluminum product and said hydrocarbon mixture enriched in internal olefins are separated from each other.

6. The process according to claim 5 further comprising subjecting said alkyl aluminum product enriched in primary linear alkyl groups derived from linear alpha-olefins in said hydrocarbon feed to controlled oxidation and hydrolysis such that linear primary alcohol is produced.

7. The process according to claim 5 further comprising reacting such separated alkyl aluminum product with propylene in the presence of a nickel or cobalt displacement catalyst under low residence-time, low isomerization displacement conditions that produce tri-n-propylaluminum and an olefin product enriched in linear 1-olefin; and separating tri-n-propylaluminum and said olefin product from each other.

8. The process according to claim 7 wherein unreacted propylene is recovered and recycled for use in reaction with separated alkyl aluminum product.

9. The process according to claim 7 wherein propylene formed as a product is recovered and used to react with the separated alkyl aluminum product.

10. The process according to claim 7 wherein tri-n-propylaluminum formed as a product is used to react selectively with linear alpha olefins in the hydrocarbon feed.

11. The process according to claim 7 wherein tri-n-propyl aluminum formed as a product is used to react selectively with linear alpha olefins in the hydrocarbon feed and wherein a deactivating amount of a lead (II) catalyst deactivator is used to deactivate said displacement catalyst in the reaction of the separated alkyl aluminum product with propylene upon completion of such reaction so as to preclude any significant isomerization of primary linear alkyl groups in said separated alkyl aluminum product.

12. The process according to claim 1 wherein said internal olefins in the hydrocarbon feed include tri-substituted olefins formed by subjecting a hydrocarbon mixture containing at least linear-alpha-olefin and vinylidene olefin to selective isomerization to convert vinylidene olefins in the mixture to trisubstituted olefins and thereby produce said hydrocarbon feed.

13. The process according to claim 1 wherein propylene formed as product is recovered and converted into tri-n-propylaluminum for use in reaction selectively with linear alpha-olefins in the hydrocarbon feed.

14. The process according to claim 1 wherein a deactivating amount of a lead (II) catalyst deactivate is used to deactivate said displacement catalyst upon completion of the displacement so as to preclude any significant isomerization, oligomerization or polymerization of primary linear alkyl groups in said alkyl aluminum product from occurring.

* * * * *